United States Patent [19]
Vogt et al.

[11] Patent Number: 5,149,633
[45] Date of Patent: Sep. 22, 1992

[54] PROCESS AND REAGENT FOR THE SPECIFIC DETERMINATION OF FRUCTOSAMINE CONTENT IN BLOOD AND SAMPLES OBTAINED FROM BLOOD

[75] Inventors: Bernd Vogt; Liselotte Schellong, both of Tutzing; Joachim Siedel, Bernried; Joachim Ziegenhorn, Starnberg, all of Fed. Rep. of Germany

[73] Assignee: Boehringer Mannheim GmbH, Mannheim, Fed. Rep. of Germany

[21] Appl. No.: 249,381

[22] Filed: Sep. 26, 1988

[30] Foreign Application Priority Data

Sep. 29, 1987 [DE] Fed. Rep. of Germany ....... 3732688

[51] Int. Cl.$^5$ .......................... C12Q 1/26; C12Q 1/54; C12Q 1/28
[52] U.S. Cl. .......................................... 435/25; 435/4; 435/14; 435/27; 435/28; 435/269; 436/34; 436/95; 436/174; 436/175; 436/904; 436/87; 436/88; 436/111
[58] Field of Search .................. 435/4, 10, 14, 25, 28, 435/269; 436/34, 63, 95, 174, 175, 904, 87, 88

[56] References Cited

U.S. PATENT DOCUMENTS

| | | | |
|---|---|---|---|
| 4,282,001 | 8/1981 | Klose et al. | 23/230 B |
| 4,314,030 | 2/1982 | Habich | 435/296 |
| 4,460,684 | 7/1984 | Bauer | 435/14 |
| 4,563,422 | 1/1986 | Deneke et al. | 435/27 |
| 4,626,511 | 12/1986 | Artiss et al. | 436/8 |
| 4,677,062 | 6/1987 | Uwajima et al. | 435/68 |
| 4,956,301 | 9/1990 | Ismail et al. | 436/87 |
| 5,002,893 | 3/1991 | Rosenthal | 436/87 |
| 5,055,388 | 10/1991 | Vogt et al. | 435/4 |

FOREIGN PATENT DOCUMENTS 0215170 3/1987 European Pat. Off. .

OTHER PUBLICATIONS

Furth, A. J., Analytical Biochemistry, vol. 175, pp. 347–360 (1988).
Martinez-Rodriguez, R., et al., Chemical Abstracts, vol. 78, No. 13, abstract No. 81826j (1972).
Singh, S. V., et al., Chemical Abstracts, vol. 105, No. 15, abstract No. 129924v (1986).
Weinryb, I., Chemical Abstracts, vol. 68, No. 17, abstract No. 75355g (1968).

*Primary Examiner*—Esther Kepplinger
*Assistant Examiner*—Toni R. Scheiner
*Attorney, Agent, or Firm*—Felfe & Lynch

[57] ABSTRACT

Process for the specific determination of the serum fructosamine content in blood or in samples obtained from blood by reaction with an appropriate color reagent and measurement of the color change thereby brought about, in which before the color reaction sample components with a non-specific reducing action and/or causing turbidity are removed and subsequently the color reagent is added at a pH value of from 10 to 12. The sample components are removed by treatment at approximately neutral pH value with a reagent composition comprising at least one enzymatic oxidation agent, optionally together with peroxidase and/or catalase and/or lipase, as well as with at least one SH group-blocking substance. A kit for the specific determination of the serum fructosamine content in blood or samples obtained from blood, comprises said reagent composition, a rebuffering reagent with a buffer which has an alkaline pH value and a color reagent for the detection of fructosamine.

27 Claims, 4 Drawing Sheets

PROCESS AND REAGENT FOR THE SPECIFIC DETERMINATION OF FRUCTOSAMINE CONTENT IN BLOOD AND SAMPLES OBTAINED FROM BLOOD

BACKGROUND OF THE INVENTION

The present invention is concerned with a process and a reagent kit for the specific determination of the serum fructosamine content in blood or in samples obtained from blood in which disturbing sample components are removed before measurement of the fructosamine content.

The serum fructosamine content is to be understood to mean the total content of non-enzymatically glycosylated serum proteins. These arise when serum glucose forms Schiff's bases via its carbonyl group with free protein amino residues which subsequently, by means of an Amadori rearrangement, are converted into fructosamines with a stable ketoamine bond.

Because of the stability of the ketoamine bond, the half-life time of the serum fructosamine is practically identical with that of the serum proteins, the half life of which is, on average, about 21 days. Corresponding investigations have been published by L. Y. Seng and M. J. Staley in *J. Clin. Chem.* 32, 560 (1986).

The extent of the fructosamine formation is proportional to the blood glucose level. As is known in the case of diabetics with insufficient dietetic and medicamentary metabolic adjustment, this can be subject to considerable variation, coupled with marked pathological phenomena.

The determination of the blood glucose provides the physician only with information regarding the metabolic state at the time of taking the blood sample. On the other hand, a long-term control regarding the metabolic state over the past 120 days is possible by determination of the glycosilated hemoglobin ($HbA_1$). Precisely because of its half-life time, the measurement of serum fructosamine is appropriate for the determination of the metabolic control of diabetics by the maintenance of diet and by therapeutic measures going back over a medium period of time of about three weeks. Therefore, in conjunction with the established clinical diagnostic parameters of blood glucose, as well as glycosylated hemoglobin ($HbA_1$), the diagnostic arsenal for the supervision of diabetics is extended by a valuable medium term parameter by means of a dependable, specific and practical method for the determination of the serum fructosamine.

A process for the determination of serum fructosamine, which in principle is easy to carry out, has been described by Baker in European Patent Specification No. 0,085,263 and by Johnson et al. in *Clin. Chim. Acta* 127, 87-95 (1982). This depends upon the fact that the ketoamine form passes over into an enol form in aqueous alkaline medium which acts reducingly on tetrazolium salts, for example nitrotetrazolium blue, and thereby provides a formazan colored material. The extent of the colored material formation measured photometrically within a definite interval of time at 37° C. is said to be proportional to the amount of fructosamine present.

In the case of the use of serum as sample material, this test is subject to disturbance since natural serum components, such as bilirubin, uric acid and SH groups, also act reducingly on tetrazolium salts. Medicaments, for example, alpha-methyldopa, decomposition products of medicaments, for example gentisic acid which is a metabolite of acetylsalicylic acid, as well as ascorbic acid, also give rise to falsified measurement results, depending upon the concentration thereof in the serum.

Even in the case of otherwise inconspicuously normal and diabetic sera these disturbances have the effect that in the case of a method comparison with, for example, the furosine/HPLC method according to Schleicher and Wieland (*J. Clin. Chem. Clin. Biochem.* 19, 81-87 (1981)), which makes possible absolute indications regarding the extent of non-enzymatic glycosylation, and the process for the determination of serum fructosamine according to Baker, there is admittedly obtained a linear correlation of the fructosamine content. However, the Baker method indicates a considerable non-enzymatic glycosylation even when this is, in fact, certainly not the case. Schematically, in a graph in which the results of the Baker method are plotted against those of the furosine/HLPC method, this has the result that, in the case of the Baker test, even when serum fructosamine is completely absent, an axis intercept occurs, the value of which corresponds to about 50% of that of the average non-diabetic (cf. FIG. 1 of the accompanying drawings).

Furthermore, serum fructosamine determinations have hitherto suffered from disturbances which are due to the total protein content which varies from sample to sample. They give rise to variations of the measurement values and thereby reduce the sensitivity of the determination process. These disturbances are known as matrix effects. Such effects are especially noticeable in the case of the addition of further protein, such as is usually the case, for example, in the preparation of standard solutions. Increasing amounts of protein slow down the reaction between fructosamine and color reagent (cf. E. J. Hindle et al., *Ann. Clin. Biochem.* 22, 84-89 (1985)).

Further difficulties arise in the case of fructosamine determinations in hyperlipemic sera. In general, in order to obtain a measurement signal which is also sufficiently great even in the case of low fructosamine concentrations, a sample/reagent volume ratio of 0.1 is necessary. In the case of excessive triglyceride concentrations, however, with such a high proportion of sample, the resultant turbidity of the test batch has a negative effect in the case of a photometric measurement, the fructosamine determination being made considerably more difficult or even prevented.

Therefore, there is still a need for a process for the specific determination of the serum fructosamine content in blood or in samples obtained from blood which does not suffer from the above-mentioned disadvantages. Consequently, it is an object of the present invention to provide such a process.

SUMMARY OF THE INVENTION

Thus, according to the present invention, there is provided an improved process for the specific determination of the serum fructosamine content in blood or in samples obtained from blood by reaction with an appropriate color reagent at a pH range of from 10 to 12 and measurement of the color change thereby brought about. In the process of this invention, sample components with a non-specific reducing action and/or which cause turbidity are removed before the color reaction. The sample is treated at approximately neutral pH value with at least one enzymatic oxidation agent, optionally together with peroxidase and/or catalase, as well as with at least one SH group-blocking substance. Subsequently, the color reagent is added at a pH in the range of from 10 to 12.

The invention also provides a kit comprising (1) a novel reagent composition comprising at least one enzymatic oxidation agent, at least one SH group blocking substance, and optionally peroxidase and/or catalase, (2) a rebuffering composition with a pH range of from 10.5 to 12.5, and (3) a color reagent preferably the color reagent (3) is dissolved in the buffer (2).

DETAILED DISCLOSURE

Figure 1:
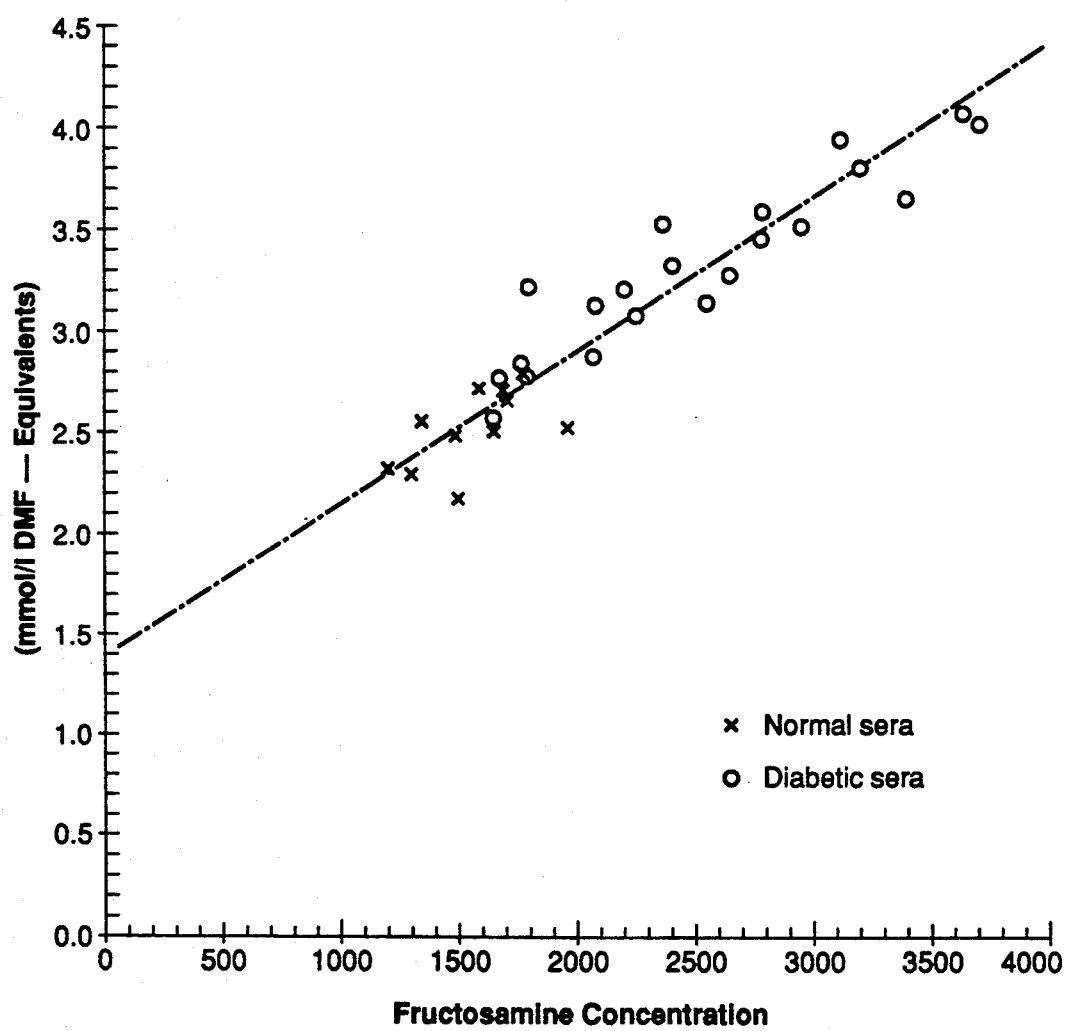
FIG. 1 is a plot showing determination of fructosamine in serum according to the method of Johnson et al., as described in Example 1.

For the removal of components with a non-specific reducing action, the sample is mixed with one or more enzymes having an oxidizing action. As enzymatically-acting oxidation agents, there are preferably added ascorbate oxidase, bilirubin oxidase and/or uricase. Peroxidase can bring about additional oxidative decomposition processes with possible formation of hydrogen peroxide, which still further increases the effectiveness of the oxidation agent or agents. Catalase optionally added serves, in particular, to remove excess hydrogen peroxide.

Especially for the investigation of lipemic samples, it has proved to be advantageous optionally to add lipase to the oxidizing-acting enzyme(s), optionally together with one or more detergents and/or salts of strong acids. With the help of such a mixture, it is possible to eliminate materials giving rise to turbidity to such an extent that the subsequent color measurement is no longer impaired. However, depending upon the sample dilution and the detergent addition, the lipemic disturbance can also be removed exclusively non-enzymatically by means of one or more detergents.

Surprisingly, we have found that by the further addition of one or more reagents blocking SH groups, there is achieved an overall correlation of the serum fructosamine method of determination according to the present invention with the furosine/HPLC comparison method without an axis intercept being attained. Thus, in the case of absence of non-enzymatically glycosilated proteins in the sample, a color reaction is indeed not observed. (See FIG. 2 of the accompanying drawings.)

SH group-blocking reagents are those which react with SH groups, many of which are described in the appropriate literature. Reference is made to the following surveys:

A. N. Glazer, R. J. Delange and D. S. Sigman, *Chemical Modification of Proteins; Laboratory Techniques in Biochemistry and Molecular Biology* (T. S. Work and E. Work, eds.) 1975;

C. H. W. Hirs and S. N. Timasheff, eds., *Modification Reactions. In: Methods in Enzymology* 25, 387–671 (1972); C. H. W. Hirs and S. N. Timasheff eds. *Chemical Modification. In: Methods in Enzymology* 47, 407–500 (1977); and R. L. Lundblad and C. M. Noyes, *Chemical Reagents for Protein Modification*, CRC Press, Boca Raton, Fla., 1984.

Available SH Blockers include, for example, iodoacetamide, iodoacetate, N-ethylmaleinimide and p-hydroxymercuribenzoate; iodoacetate has proved to be especially useful for the process according to the present invention.

With the help of the above-mentioned substances for the removal of disturbing components, the measurement variations, known as matrix effects, due to varying amounts of total protein in the sample, are substantially suppressed or completely removed. Thus, the prerequisite for a correct protein correction by formation of the quotient fructosamine/total protein is provided.

For removing sample components with a non-specifically reducing action and/or which give rise to turbidity, it has proved to be advantageous to incubate the sample with a solution which contains oxidizing-acting enzymes, as well as at least one lipid-cleaving enzyme and SH group-blocking substance, as well as possibly at least one detergent and/or salt of a strong acid in an appropriate non-reducing buffer. For the preparation of this solution, there can be used all buffer substances which themselves do not act reducingly and the buffering action of which lies approximately at the neutral pH value. It has proved to be advantageous to use a pH range of from 6 to 9, preferably of from 7 to 8.5 and most preferably of from 7.5 to 8. The buffer concentration is advantageously from 10 to 100 mmole/liter and preferably of from 20 to 70 mmole/liter. Aqueous potassium phosphate buffer has proved to be especially advantageous.

The concentration of the added enzymes depends upon the concentration of the disturbing compounds to be removed. These enzyme concentrations are usually from 0.01 to 10,000 U/ml. Preferred concentration ranges are, for example, the following:

| | |
|---|---|
| uricase | 1–15 U/ml. |
| bilirubin oxidase | 0.05–5 U/ml. |
| ascorbate oxidase | 2–20 U/ml. |
| lipase | 0.5–5 U/ml. |
| peroxidase | 0.5–5 U/ml. |
| catalase | 100–10,000 U/ml. |

Especially preferred concentration ranges for these enzymes are the following:

| | |
|---|---|
| uricase | 2–10 U/ml. |
| bilirubin oxidase | 0.1–1 U/ml. |
| ascorbate oxidase | 5–15 U/ml. |
| lipase | 1–3 U/ml. |
| peroxidase | 1–3 U/ml. |
| catalase | 500–2,000 U/ml. |

As SH group-blocking substances, there can, in principle, be used all reagents known for this purpose from the literature, for example iodoacetamide, iodoacetate, N-ethylmaleinimide and p-hydroxymercuribenzoate; iodoacetamide has proved to be especially useful. The preferred concentration range for the SH blockers is from 0.5 to 500 mmoles/liter and especially from 5 to 50 mole/liter.

Apart from cationic substances, the detergents can also be anionic or non-ionic substances. Preferred anionic detergents include alkali metal and alkaline earth metal salts of bile acids and conjugates thereof. Preferred concentrations of anionic detergents are from 2 to 10 mmole/liter. It has proved to be preferable to use sodium cholate in a concentration of from 4 to 6 mmole/liter.

As non-ionic detergents, a broad palette of substances is available. In particular, linear or branched-chained alkyl and alkylaryl alcohol polyglycol ethers containing 8 to 20 carbon atoms in the alcohol part and 4 to 15 glycol units per molecule have proved to be useful; linear and branched-chained alkyl alcohol polyglycol ethers with 8 to 12 carbon atoms in the alcohol part and 4 to 8 glycol units per molecule have proved to be especially advantageous.

For the process according to the present invention for the specific determination of the serum fructosamine content, there can be used non-ionic detergents which, with regard to the structure of the alcohol part, are uniform or can be a mixture of several polyglycol ethers which differ with regard to the structure of the alcohol part. Appropriate non-ionic detergents include, for example, Oxetal® ID 104 (Zschimmer & Schwarz, Lahnstein, Federal Republic of Germany), Product RT 240® (Zschimmer & Schwarz, Lahnstein, Federal Republic of Germany), Lutensol® ON 50, ON 60, ON 70 (BASF, Ludwigshafen, Federal Republic of Germany), as well as Soprofor® D/916 (Rhone-Poulenc, France). The concentration of non-ionic detergent which is used according to the present invention for the removal of sample components with a non-specific reducing action and/or which cause turbidity can be from 0.05 to 15% by weight, a concentration range of from 0.1 to 5% by weight having proved to be preferable.

The turbidity-removing action can be further increased by higher ionic strengths in the reaction solution. For this purpose, there have proved to be useful additions of salts of strong acids which also remain in solution in the alkaline pH range, the alkali metal and alkaline earth metal salts of hydrochloric and sulphuric acid being preferred. Potassium chloride and sodium chloride are especially preferably used. The concentration of the added salts of strong acids can be from 20 to 100 mmole/liter, the salts preferably being added in a concentration of from 40 to 60 mmole/liter.

The removal of sample components with a non-specific reducing action and/or which cause turbidity takes place at a temperature of from 25° to 40° C. and preferably at about 37° C. over a period of time of from 1 to 15 minutes and preferably of from 2 to 6 minutes. The period of time of the incubation to be chosen depends upon the amount of sample components with a non-specific reducing action and causing turbidity and the amount of additives used for the removal thereof.

Since the incubation for the removal of the sample components with a non-specific reducing action and/or which cause turbidity is, because of the pH optimum of the enzymes used, carried out at approximately neutral pH value but the color reaction between the color reagent and the fructosamine takes place at a pH value of from 10 to 12, it is necessary to rebuffer after the incubation has taken place. The increasing of the pH value takes place by means of a buffer, the pH value of which lies somewhat above the pH value to be adjusted. A buffer with a pH value of from 10.5 to 12.5 and preferably of from 10.7 to 12.2 is particularly advantageous.

For this purpose, it is preferred to use a carbonate buffer, the concentration of which is from 150 to 300 mmole/liter and preferably from 180 to 220 mmole/liter.

The reducing action of the fructosamine can be made visible in known manner by the addition of a color reagent in the alkaline range. For this purpose, there is preferably used a tetrazolium salt, the formazan colored material formation of which can be monitored visually or photometrically. As tetrazolium salts, those are preferred which are described in *Methods of Enzymatic Analysis* (H. U. Bergmeyer, ed., 3rd ed., pub. Verlag Chemie, Weinheim, Federal R®public of Germany, Volume I, p. 200 (1983)), nitrotetrazolium blue (NBT) and 3-(4',5'-dimethylthiazolyl-2)-2,4-diphenyltetrazolium bromide (MTT) being especially preferred. The color reagent can be added to the test batch not only after the rebuffering but also simultaneously with the buffer. For this purpose, it has proved to be preferable to dissolve the color reagent in the buffer required for the rebuffering. For tetrazolium salts, there have proved to be useful concentrations of from 0.2 to 2 mmole/liter and especially of from 0.4 to 1.5 mmole/liter.

For the rebuffering after removal of sample components with a non-specific reducing action and/or causing turbidity, there is added such an amount of buffer that the pH value of the test batch in the case of the presence of the color reagent, has a pH value of from 10 to 12 and preferably of from 10.3 to 10.6.

The rebuffered solution is incubated at a temperature of from 25° to 40° C. and preferably at about 37° C. The color change due to the reduction of the color reagent is monitored photometrically over a definite period of time and preferably for 1 to 15 minutes after rebuffering. A first measurement is carried out 1 to 10 minutes after the rebuffering and a last measurement 2 to 15 minutes after the rebuffering. Depending upon the requirements, two or more measurements can be carried out. The time intervals between the two measurements are variable. They can be chosen depending upon the apparatus employed and can be in a range of from a few seconds up to a few minutes.

It is preferable to compare the measurement values obtained with those of a standard solution, appropriate standard solutions being known. For example, for this purpose there can be used the standard described by Johnson et al. in *Clin. Chim. Acta* 127, 87–95 (1982), which is based upon a matrix of human albumin with definite additions of a synthetic fructosamine. As synthetic fructosamine, there can be used 1-desoxy-1-morpholinofructose (DMF). The serum fructosamine concentration determined in the sample is, in the case of the use of this standard, given in DMF units. As a standard, there can also be used a human serum albumin or a bovine serum albumin or other protein with, in each case, a known degree of glycosilation.

Surprisingly, the process according to the present invention also permits the sample/reagent volume ratio of 0.1, which is usual according to the process of Johnson et al., to be considerably reduced without, in the case of the same time interval and incubation at the same temperature, the measurement signal with a definite amount of fructosamine analogue used as sample becoming significantly smaller in comparison with the method described by Johnson et al. If, as fructosamine analogue, there is used, for example DMF, the sample/- reagent volume ratio can be reduced to 0.02 without the sensitivity of the measurement being reduced.

The process according to the present invention for the determination of fructosamine in blood or in samples obtained from blood, in which sample components with a non-specific reducing action and/or which cause turbidity are removed with the help of at least one enzyme and SH blocker, as well as possibly at least one detergent and/or salt, can be carried out not only in solution. It can readily be transferred to determination processes using dry chemical test carriers. The enzymes and SH blockers, as well as possibly at least one detergent and/or salt and possibly further adjuvant materials, are, for this purpose applied in known manner to solid carriers. Appropriate solid carriers, as well as processes for the application of these materials or material mixtures to such carriers, are known to persons skilled in the art. As carrier materials, there can be used, for example, all possible absorbent materials, such as paper, fleece and the like. The materials to be applied can be taken up in one or more impregnation solutions, the carriers being impregnated or sprayed with these solutions and subsequently dried.

Another possibility is to introduce the enzymes and SH blockers, as well as possibly detergents and/or salts and possibly further adjuvant materials, into reagent filems. For this purpose, the substances or substance mixtures are worked up to give reagent films, for example according to the processes described in Federal Republic of Germany Patent Specification Nos. 1,598,153 and 2,910,134.

For the removal of disturbing sample components with a non-specific reducing action and/or which cause turbidity, the sample to be measured is first brought into contact with a carrier which contains the enzyme(s) and SH group-blocking reagent(s), as well as possibly at least one detergent and/or salt. After sufficient contact, the pretreated sample is transferred to a layer which contains the further reaction components necessary for the color reaction. The color change thereby brought about can be measured in known manner photometrically, for example, reflectometrically. With regard to the time interval for the pre-reaction and for the color reaction, there apply the statements made hereinbefore.

The present invention also provides a reagent kit for the specific determination of the serum fructosamine content in blood or samples obtained from blood, comprising (1) a novel reagent composition for the removal of sample components with a non-specific reducing action and/or which cause turbidity, and (2) a rebuffering reagent with a buffer which has an alkaline pH value, and (3) a color reagent for the detection of fructosamine. Preferably the color reagent (3) is dissolved in the rebuffering agent (2) and therefore the kit is essentially a two-component kit. The reagent composition (1) for removal of sample components with a non-specific reducing action and/or which cause turbidity in a buffer with substantially neutral pH value contains at least one enzymatic oxidation agent, as well as possibly peroxidase and/or catalase and/or lipase, as well as possibly at least one detergent and/or salt of a strong acid as well as at least one SH group-blocking substance and possibly conventional additives. The buffer of the rebuffering reagent (2) preferably has a pH value in the range of from 10.5 to 12.5. The above reagent kit contains all the components necessary for carrying out the process according to the present invention.

The enzymatic oxidation agents are understood to be, in particular, ascorbate oxidase, bilirubin oxidase and uricase.

SH group-blocking reagents are especially iodoacetamide, iodoacetate, N-ethylmaleinimide and p-hydroxymercuribenzoate and compounds related thereto.

The detergents contained in the reagent composition (1) according to the present invention for the removal of sample components with a non-specific reducing action and/or which cause turbidity in blood or in samples obtained from blood can be anionic or non-ionic. As anionic detergents, there are especially preferred alkali metal and alkaline earth metal salts of bile acids and the conjugates thereof. For non-ionic detergents there is available a broad palette of compounds. Linear and branched-chained alkyl and alkylaryl alcohol polyglycol ethers with 8 to 20 carbon atoms in the alcohol part and 4 to 15 glycol units per molecule have proved to be preferable. However, in addition, the added detergents can also cationic, for example, a hydroxyethylalkylammonium phosphate, such as Dehyquart® SP of the firm Henkel, Düsseldorf, Federal Republic of Germany.

A mixture containing the enzymes peroxidase and uricase, the SH blocker iodoacetamide, a non-ionic detergent, for example, Lutensol® ON 60, as well as the anionic detergent cholate, is quite especially effective.

As salts of strong acids, the alkali metal and alkaline earth metal salts of hydrochloric and sulphuric acid have proved to be appropriate, potassium chloride and sodium chloride being especially preferred.

The buffer required for the achievement of substantially neutral pH value of the reagent composition according to the present invention has a pH value in the range of 6 to 9, preferably of from 7 to 8.5 and more preferably of from 7.5 to 8.0. The buffer concentration is preferably from 10 to 100 mmole/liter and especially from 20 to 70 mmole/liter. Aqueous potassium phosphate buffer has proved to be especially advantageous.

The following examples are given for the purpose of illustrating the process and reagent kit according to the present invention:

EXAMPLE 1 (Prior Art)

Determination of fructosamine in serum according to the method of Johnson et al. on an automatic analyzer.

Reagent composition:
0.1 mole/liter sodium carbonate buffer (pH 10.35)
0.25 mmole/liter nitrotetrazolium blue.

Carrying out of the determination:
20 $\mu$l. of sample are mixed with 200 $\mu$l. of reagent and 50 $\mu$l. of water (diluent) and the extinction determined dependent upon time at 37° C. on a Cobas Bio® automatic analyzer (Hoffmann-La Roche, Basel, Switzerland). For the determination of the fructosamine concentration, the kinetics are evaluated between the 10th and 15th minute after addition of the reagent.

These results are plotted against the measurement values which have been obtained with the furosine/HPLC method (*J. Clin. Chem. Clin. Biochem.* 19, 81-87 (1981)). As HPLC measurement values, there are, in each case, used relative peak surface units (see FIG. 1 of the accompanying drawings).

The furosine/HPLC method is also used as reference method in the following examples.

EXAMPLE 2

Determination of fructosamine in serum by the process according to the present invention in an automatic analyzer.

A) Composition:

| Component | Concentration |
|---|---|
| a) Reagent composition (1): | |
| potassium phosphate buffer (pH 8.0) | 50 mmole/liter |
| potassium chloride | 50 mmole/liter |
| sodium cholate | 5.6 mmole/liter |
| Lutensol ® ON 60 (BASF, Ludwigshafen, Federal Republic of Germany) | 2.5% by weight |
| uricase | 4 U/ml. |
| peroxidase | 2 U/ml. |
| lipase | 2 U/ml. |
| iodoacetamide | 20 mmole/liter |
| b) Rebuffering and Color Reagents: | |
| sodium carbonate buffer (pH 10.9) | 200 mmole/liter |
| nitrotetrazolium blue salt (NBT) | 0.5 mmole/liter |

B) Carrying out of the test:

The tests are carried out on a Hitachi 704 automatic analyzer.
Wavelength 546 nm
temperature 37° C.
layer thickness 10 mm. (semimicrocuvette)
Into cuvettes are pipetted:

| | sample (p) | reagent blank (RL) |
|---|---|---|
| reagent composition (1) | 175 μl. | 175 μl. |
| sample | 7 μl. | — |
| distilled water | — | 7 μl. |

After incubation for 5 minutes at 37° C., there are then admixed:

| | | |
|---|---|---|
| rebuffering and color reagent | 175 μl. | 175 μl. |

After again incubating, the kinetics of the colored material formation ($\Delta E_P$ or $\Delta E_{RL}$) are measured within the course of a definite interval of time $\Delta t$ (8 to 10 minutes).

In a manner corresponding to that described above for the sample, there is measured a standard solution (S) with known fructosamine content and from the thus obtained values there is calculated by means of a rule of three, the fructosamine concentration of the sample.

Figure 2:
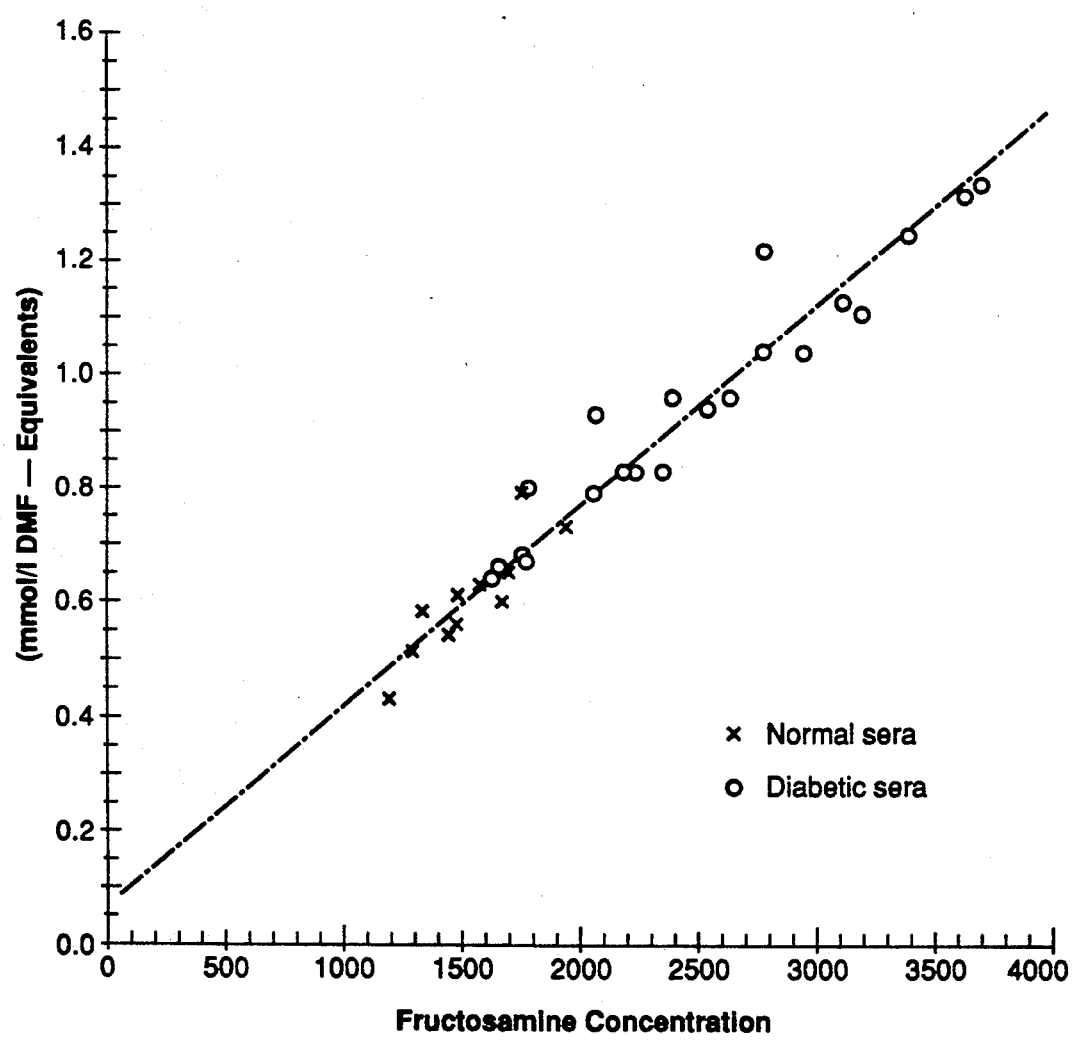
FIG. 2 is a plot showing determination of fructosamine in serum according to the method of this invention as described in Example 2.

In FIG. 2 of the accompanying drawings, the measurement values obtained are plotted against those determined with the furosine/HPLC method.

A comparison of the results of Example 1 and Example 2 show that, with the process according to the present invention in comparison with the prior art, there is obtained an improvement of the correlation of the measurement values and a substantial reduction of the axis intercept in the case of comparison with the HPLC reference method.

EXAMPLE 3

Determination of serum fructosamine as in Example 2 but without iodoacetamide.

Figure 3:
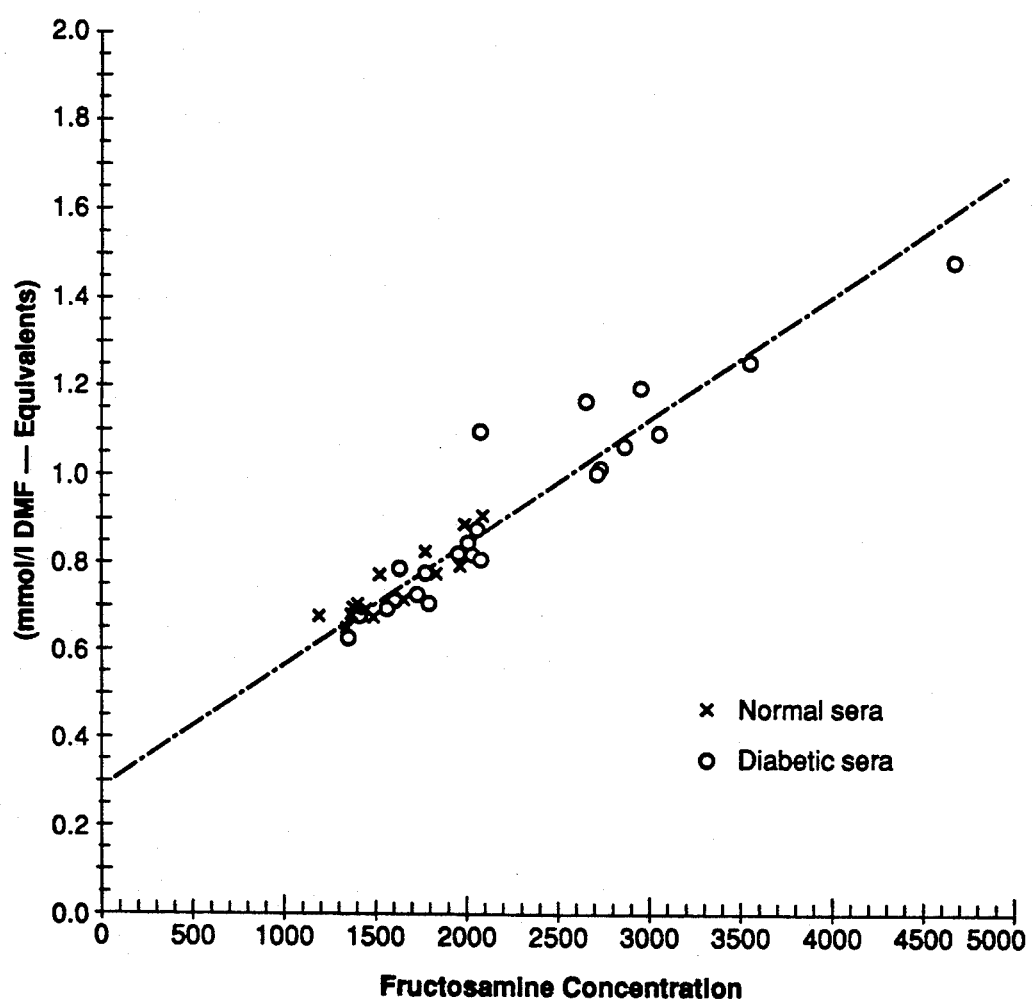
FIG. 3 is a plot showing determination of fructosamine in serum as described in Example 3.

In FIG. 3 of the accompanying drawings, the measurement values thus obtained are plotted against those determined with the furosine/HPLC method.

Although FIG. 3, in comparison with FIG. 1, shows a substantially reduced axis intercept and thus already permits a substantially more dependable statement of the actual serum fructosamine content, a comparison of FIG. 3 with FIG. 2 clearly indicates the additional suppressing influence of the SH group-blocking reagent.

EXAMPLE 4

Figure 4:
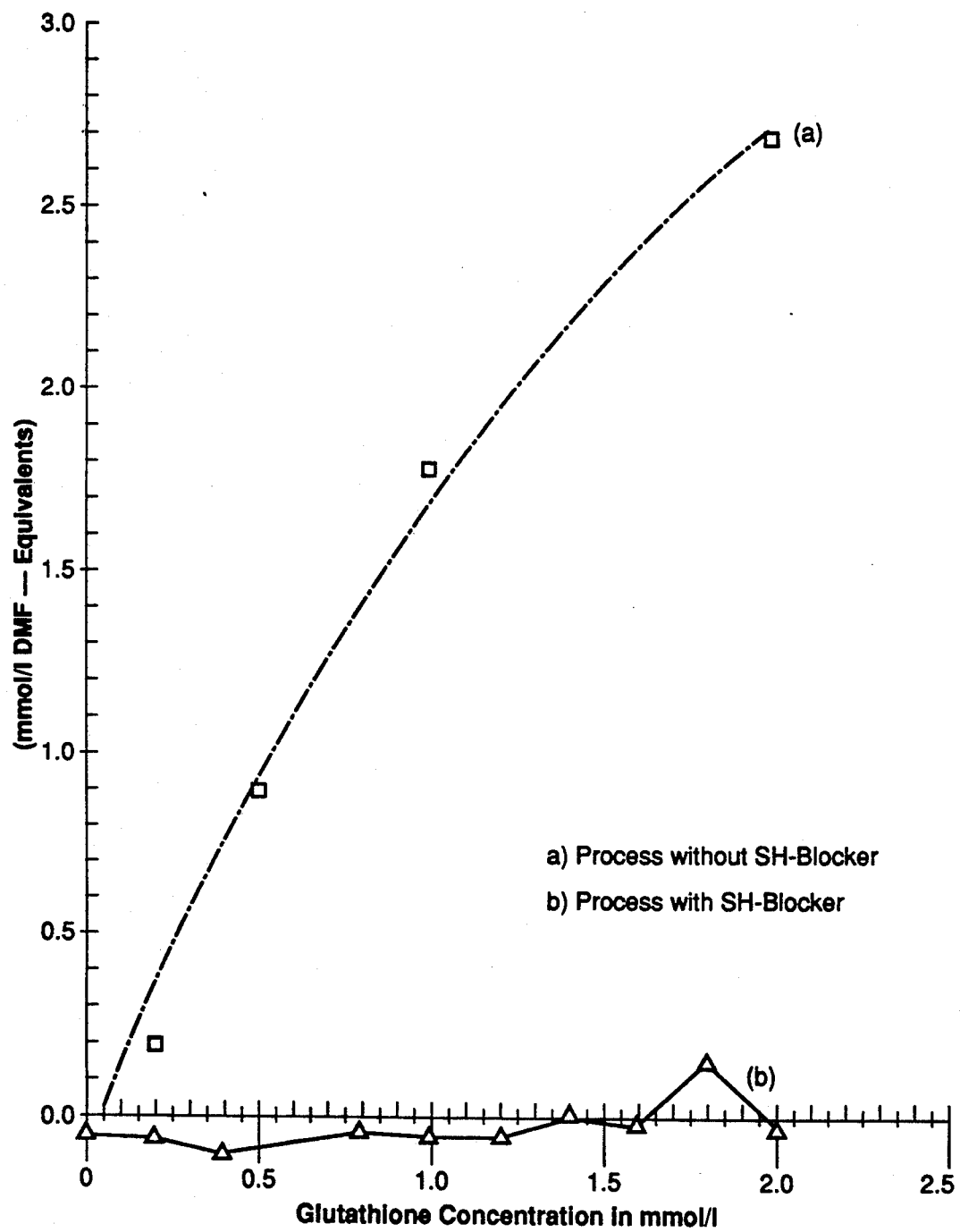
FIG. 4 is a plot showing the influence of increasing amounts of glutathion on the determination of serum fructosamine, as described in Example 4.

The influence of increasing amounts of SH groups, for example of glutathione, on the determination of serum fructosamine is illustrated in FIG. 4 of the accompanying drawings.

In (a), the reagent composition is as in Example 3 and in (b) the reagent composition is as in Example 2.

In each case, the measurement of the fructosamine content takes place in the manner described in the corresponding Examples 2 and 3. It is ascertained that an SH group blocking dependably overcomes the disturbance. Without the addition of SH group-blocking reagents, nonenzymatically glycosilated protein is simulated by SH groups.

Various embodiments of the compositions and methods described and claimed herein will, of course, be evident to the skilled artisan. The examples given herein are in no way to be construed as limitative of the broad disclosure.

While there have been described what are at present considered to be the preferred embodiments of this invention, it will be obvious to one skilled in the art that various changes and modifications may be made therein without departing from the invention, and it is, therefore, aimed to cover all such changes and modifications as fall within the true spirit and scope of the invention.

We claim:

1. In a process for the specific determination of the serum fructosamine content on a blood sample or in sample obtained from blood by reaction with a tetrazolium salt at an alkaline pH and measurement of the resultant color change, the improvement comprising:
   (i) removing components which cause non-specific reduction of the tetrazolium salt or which cause turbidity by treating the sample with a reagent composition comprising at least one oxidoreductase and at least one SH group blocking agent in an amount sufficient to prevent non-specific reduction of the tetrazolium salt from 1 to 15 minutes, the pH of said composition being from 6 to 9,
   (ii) bringing the sample to a pH of from 10 to 12 with a rebuffering reagent prior to or simultaneously with the reaction with the tetrazolium salt, and
   (iii) determining color formation or color change from 1 to 15 minutes after adding said rebuffering reagent.

2. A process according to claim 1 in which the rebuffering reagent is added to the sample simultaneously with the tetrazolium salt.

3. A process according to claim 1 in which the pH of the reagent composition is from 7.0 to 8.5 and the pH of the rebuffering reagent is from 10.5 to 12.5.

4. A process according to claim 1 in which the pH of the reagent composition is from 7.5 to 8.0 and the pH of the rebuffering reagent is from 10.7 to 12.2.

5. A process according to claim 1 in which the pH of the rebuffered sample is from 10.3 to 10.6.

6. A process according to claim 1 in which the oxidureductase is ascorbate oxidase, bilirubin oxidase or uricase.

7. A process according to claim 1 in which the SH group blocking agent is iodoacetamide, iodoacetate, N-ethylmaleinimide or p-hydroxymercuribenzoate.

8. A process according to claim 1 in which the SH group blocking agent is iodoacetamide.

9. A process according to claim 1 in which the reagent composition additionally comprises peroxidase or catalase.

10. A process according to claim 1 in which the reagent composition additionally comprises at least one detergent.

11. A process according to claim 10 in which the detergent is a non-ionic or anionic detergent.

12. A process according to claim 1, in which the reagent further comprises a detergent and a salt of a strong acid.

13. A process according to claim 12 in which the detergent is an ionic or non-ionic detergent and the salt of a strong acid is an alkali metal or alkaline earth metal salt of hydrochloric or sulfuric acid.

14. A process according to claim 13 in which the salt is potassium chloride or sodium chloride.

15. A process according to claim 1 in which the reagent composition additionally comprises lipase.

16. A process according to claim 1 in which the reagent composition comprises uricase, bilirubin oxidase, ascorbate oxidase, lipase, peroxidase or catalase and at least one SH group blocking agent.

17. A process according to claim 16 in which the SH group blocking substance is iodoacetamide.

18. A process according to claim 17 n which the reagent composition additionally comprises an ionic or non-ionic detergent and an alkali metal chloride.

19. A kit for the specific determination of the serum fructosamine content in a blood sample or in a sample obtained from blood which comprises
  (1) a tetrazolium salt,
  (2) a reagent composition comprising at least one oxidoreductase and at least one SH group blocking agent in an amount sufficient to prevent nonspecific reduction of the tetrazolium salt, the pH of said reagent composition being from 6 to 9, and
  (3) a rebuffering reagent having a pH of from 10.5 to 12.5.

20. A kit according to claim 19 in which said tetrazolium salt is dissolved in the rebuffering reagent.

21. A kit according to claim 19 in which the pH of the reagent composition is from 7 to 8.5 and the pH of the rebuffering reagent is from 10.7 to 12.2.

22. A kit according to claim 19 in which the reagent composition additionally comprises peroxidase or catalase or lipase.

23. A kit according to claim 19 in which the oxidoreductase is ascorbate oxidase, bilirubin oxidase or uricase.

24. A kit according to claim 19 in which the SH group blocking agent is iodoacetamide, iodoacetate, N-ethylmaleinimide or p-hydroxyme ribenzoate.

25. A kit according to claim 19 in which the SH blocking agent is iodoacetamide.

26. A kit according to claim 22 which additionally comprises a cationic, anionic or non-ionic detergent and additionally comprises an alkali metal or alkaline earth metal salt of hydrochloric or sulfuric acid.

27. A kit according to claim 19 in which the reagent composition comprises peroxidase, uricase, lipase, iodoacetamide, a non-ionic detergent and an anionic detergent.

* * * * *